US006302112B1

(12) United States Patent
Ciolfi

(10) Patent No.: US 6,302,112 B1
(45) Date of Patent: Oct. 16, 2001

(54) DEVICE FOR INDUCING A PROMPT RECOVERY FROM HICCOUGHS

(76) Inventor: Giancarlo Ciolfi, Via dello Scalo Prenestino, 10-00159 Rome (IT)

(*) Notice: Subject to any disclaimer, the term of this patent is extended or adjusted under 35 U.S.C. 154(b) by 0 days.

(21) Appl. No.: 09/486,591

(22) PCT Filed: Jun. 5, 1998

(86) PCT No.: PCT/IT98/00150

§ 371 Date: Mar. 1, 2000

§ 102(e) Date: Mar. 1, 2000

(87) PCT Pub. No.: WO99/11217

PCT Pub. Date: Mar. 11, 1999

(30) Foreign Application Priority Data

Sep. 1, 1997 (IT) .......................................... RM97A0524

(51) Int. Cl.$^{7}$ .................................................. A61B 19/00

(52) U.S. Cl. ......................................... 128/897; 215/386

(58) Field of Search ............................ 210/14; 165/119; 220/706, 19; 75/53; 427/230; 99/326; 250/461; 239/403; 215/386; 222/566

(56) References Cited

U.S. PATENT DOCUMENTS 4,210,141 7/1980 Brockman et al. .

FOREIGN PATENT DOCUMENTS

| | | |
|---|---|---|
| 287382 | 9/1915 | (DE) . |
| 215244 | 5/1924 | (GB) . |
| 2190596 | 11/1987 | (GB) . |
| 1133182 * | 10/1980 | (IT) . |
| WO 97/07724 | 3/1997 | (WO) . |

OTHER PUBLICATIONS

Hansen, B.J., Persistent Postoperative Hiccups: a Review, Acta Anaesthesiologica Scandinavica, vol. (Issue) 37 (7), pp. : 643–646, 1993.*

* cited by examiner

*Primary Examiner*—Eric F. Winakur
*Assistant Examiner*—Nikita R Veniaminov
(74) *Attorney, Agent, or Firm*—Young & Thompson

(57) ABSTRACT

The device includes a circular disk, having a plurality of holes, whereon a cylindrical stick or peg is fixed. The axes of the disk and of the stick or peg are parallel and do not coincide with each other. The holes allow the passage of liquids through the disk, in order to generate turbulences and air sacks. The device can be placed inside a drinking glass or a feeding bottle.

5 Claims, 4 Drawing Sheets

DEVICE FOR INDUCING A PROMPT RECOVERY FROM HICCOUGHS

FIELD OF THE INVENTION

The present invention relates to the health service field and to sanitary equipment, more particularly to a device that induces a prompt recovery from hiccoughs.

BACKGROUND OF THE INVENTION

In the Therapeutic Handbook, hiccoughs are defined as an "involuntary spasmodic contraction of the diaphragm, caused by an incipient inspiration which is suddenly controlled by the closing of the glottis which causes its characteristic noise".

From aetiology, which studies causes of illnesses, we know that generally hiccoughs have got no medically relevant meaning and they last for not long; the cause for their occurrence is often unknown.

The pathologies wherein this phenomenon may appear are diverse. Among them there are found: epidemic encephalitis, oesophagitis, gastritis, dyspepsias, aerophagia, hepatitis, pancreatitis, peritonitis, alcoholism, mediastinum tumours, pneumonia, pleuritis and hysteric neurosis.

In any case it is a disease with a marked social impact as it does not only involve the people that are affected by it, but also those people who are close to them. To this purpose attention is for example drawn to a person who is affected by hiccoughs during a theatrical event, a concert or an opera, where silence is mandatory, or on a public means of transport.

The occurrence of persistent hiccoughs is also very annoying and problematic for several professional categories like for example singers, television programme hosts, journalists, and so on.

Persistence of hiccoughs can also stop the subject from dedicating the due attention to his professional activity, determining an increase in the possibility of accidents on the working place.

Currently, remedies can be categorised into two groups: one of a semi-empirical type and one of a therapeutical type.

A) Classical maneuvres aimed at disrupting the occurrence of hiccoughs:
   1. Compression of the ocular bulbs
   2. Compression with the two thumbs of the two nervi phrenici situated behind the sternoclavicular articulations.
   3. Rhytmic traction of the tongue.
   4. Warm and cold applications in the epigstric region.
   5. Counting without breathing.

B) Symptomatic therapy:
   a) Plasil (metochlorpropamide)
   b) Largactil (Chlorpromazin)
   c) Magistral solution with an analgesic action localised to the gastric mucose (a tablespoon in the evening) based on sulphurous ether (g 3.0)+mint water (70.0 g)+distilled water (70.0 g)+syrups of various nature (45.0 g).
   d) Application of high frequency current or ultrasounds or 0.5% procain to the nervus phrenicus at neck's height.
   e) surgical lesion of one of the two nervi phrenici.
   f) Tranquillisers (in their hysteric base forms).

Said remedies are almost always annoying and heavy for anyone and they become real tortures for children, particularly for those who are not self-sufficient.

Besides that, said remedies do not often accomplish their aim, to the detriment of the subjects affected by the disease, and at times even of those that are around them.

Unfortunately, after weaning, not all toddlers are able to execute what adults have told them to do. This also happens in the case of adults that suffer from bad physical and/or psychiatric handicaps.

Furthermore it is known that in certain cases hiccoughs can last for several hours, if not even days.

SUMMARY OF THE INVENTION

A first aim of the present invention is therefore that of providing a device which is able to rapidly induce recovery from hiccoughs both in adults and children and in people who are not self-sufficient.

A second aim of the present invention is that of finding an absolutely atoxic device that guarantees the highest safety when used in the food industry field.

The inventor started from the observation that a liquid of any type contained in a container provided with a choking corresponding to the outlet hole (a bottle for example), is poured, and a whirl and some turbulences form and give way to extremely small air sacks.

It is clear that if the container's outlet consists of a choking provided with more than one hole, pouring its content many whirls will form and the ensuing development of air-sacks will be proportional to the number of holes present in the structure.

Having well clarified that point, recalling the empirical remedies traditionally proposed up to that moment and following the experiments that he has carried out, he surprisingly observed that if a subject effected by hiccoughs takes a few sips of a liquid, preferably water, from a glass wherein there is found to be placed a device consisting of circular disk with holes on which a straight cylindrical stick or peg is fixed, hiccoughs disappear after a few seconds.

It is therefore an object of the present invention to provide a device made of an atoxic material, preferably made of steel, comprising a punched circular disk on which a straight cylindrical stick or peg is fixed.

According to a peculiar aspect of the present invention the disk and the peg have got parallel but not coinciding axes. This to the purpose of preventing turbulence from swirling when the liquid passes through each single hole of said disk.

Advantageously, the present invention which is described in the foregoing can be applied and used in situations of whatever type, in a rapid manner. Furthermore it is devoid of counterindications.

BRIEF DESCRIPTION OF THE DRAWINGS

A better understanding of the present invention will be gained on reading the following detailed description and with reference to the appended figures that, only by way of not limiting example, illustrate some preferred embodiments thereof.

In the drawings.

DETAILED DESCRIPTION OF PREFERRED EMBODIMENTS

As it was already briefly mentioned above, and with reference to the figures, the device object of the present invention substantially consists of a circular punched disk 1, whereon a cylindrical stick or peg 2 with parallel and not coinciding symmetry axes is fixed.

Figure 1:
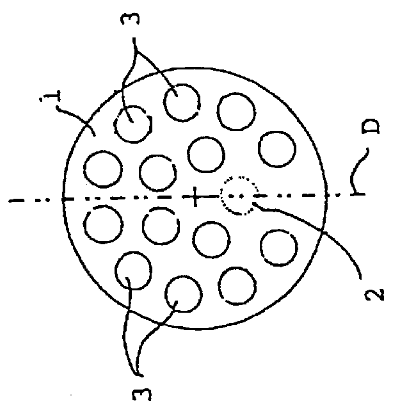
FIGS. 1, 2 and 3 are respectively a plan view from below, a side elevation view and a front view of the device object of the present invention.
Figure 2:
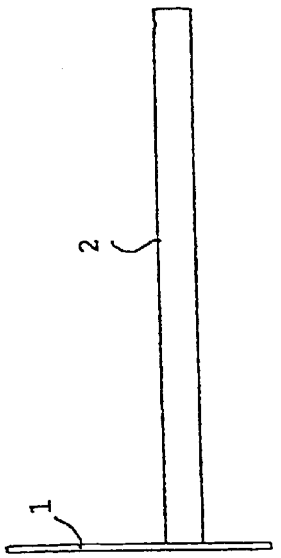
Figure 3:
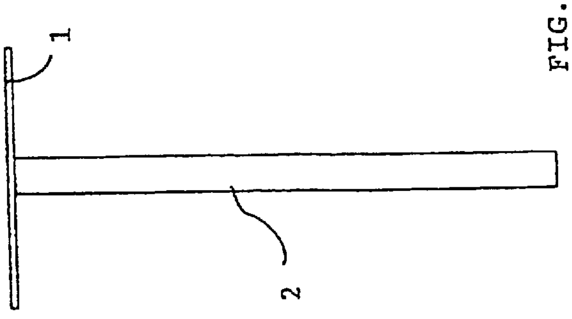
Figure 4:
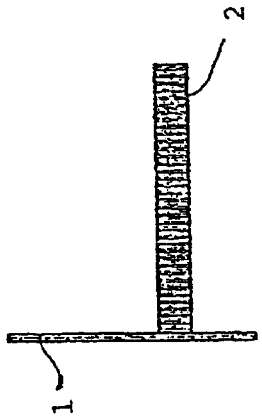
FIG. 4, which is similar to FIG. 3, shows the device object of the present invention in a shorter length configuration.
Figure 5:
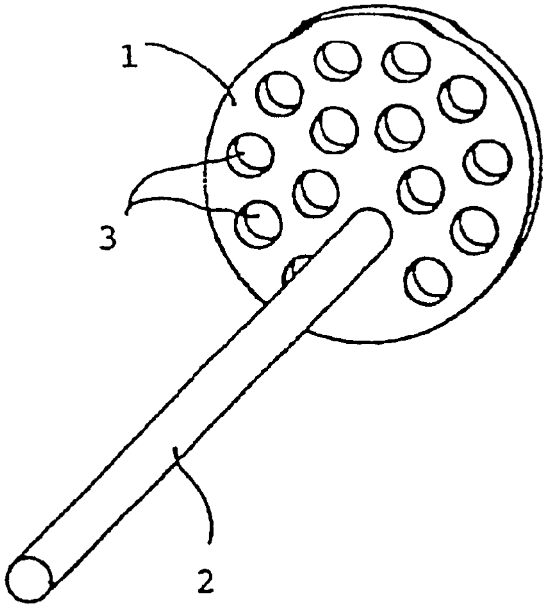
FIGS. 5 and 6 are perspective views of the device object of the present invention as conceived with two different lengths.
Figure 6:
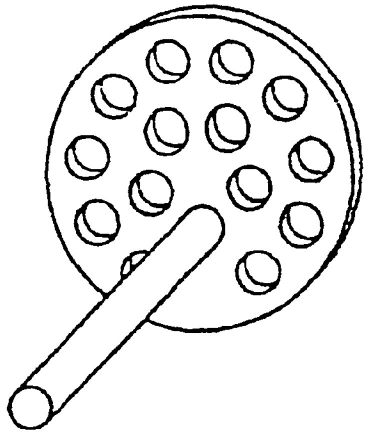
Figure 7:
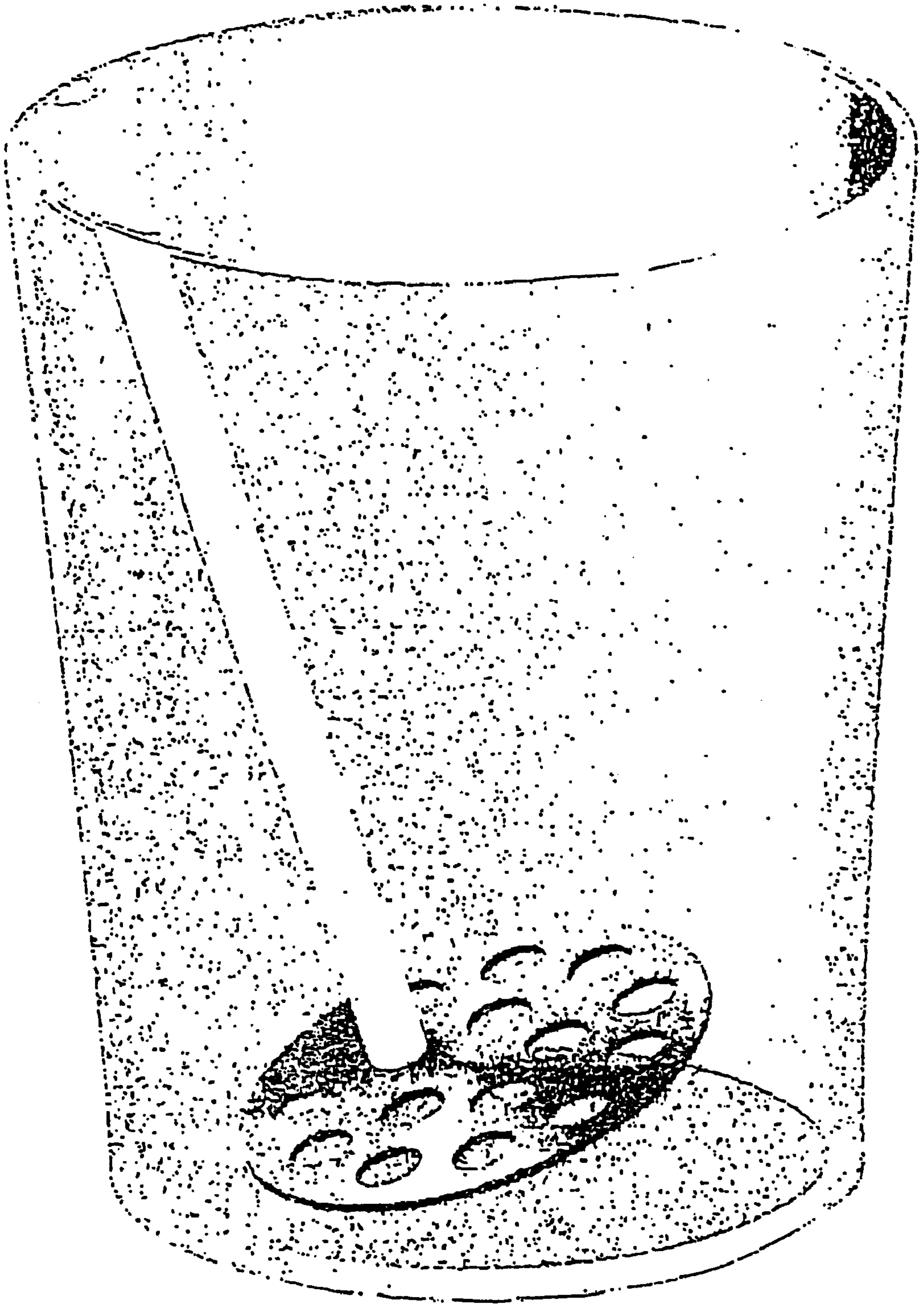
FIG. 7 illustrates a first embodiment of the present invention for its utilization inside a glass.

According to the present invention and with particular reference to FIGS. 5 and 7, in case the subject affected by hiccoughs is able to drink from a glass, this is then enough to place the device object of the present invention into the glass in such a way that punched disk 1 contacts the bottom of said glass only with a stretch of its circumference. In so doing there is a passage left available for the liquid to flow through the holes, in order to generate those turbulences that cause the formation of the air sacks.

At this stage, forcing stick 2 to lean onto the side of the glass with two fingers, and drinking the liquid therein contained as normal, there will occur recovery from hiccoughs after taking a few sips.

Advantageously the device object of the present invention can be used without any problems even by children, including babies and toddlers, when it is necessary to use a feeding-bottle.

Figure 8:
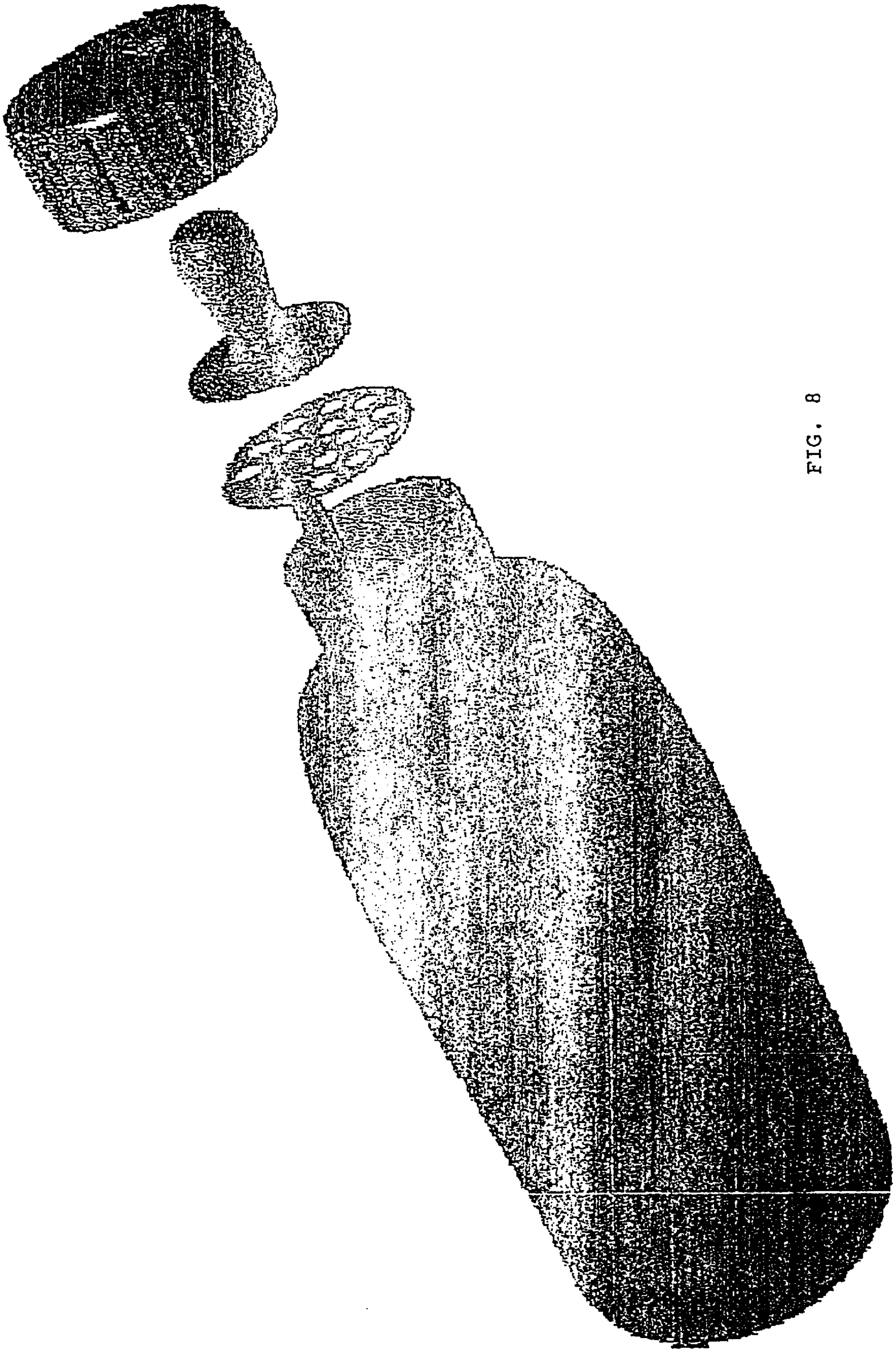
FIG. 8 shows the device object of the present invention as it is applied to a feeding-bottle.

It is in fact sufficient to place the device on the feeding-bottle so that stick or peg 2 points towards the inside of the bottle and punched disk 1 is located between the base of the nipple and the mouth of the bottle itself (FIG. 8).

Even in this case, a few sips are enough for a prompt recovery from hiccoughs to occur.

As it is shown in the drawings, the length of stick or peg 2 can vary according to the specific needs, for example according to the height of the glass or of the feeding-bottle.

In both applications, the presence of the device that is being described causes the formation of turbulent motions and of very little bubbles within the liquid that is being drunk. Consequently, the person that drinks is also forced to intake a small amount of air during swallowing and that gives way to the termination of that annoying disturb.

In the embodiment shown, within the device there is provided a disk with a 36 mm diameter and a 1 mm thickness, having 14 holes (to which reference number 3 was given) with a 5 mm diameter, located along two concentric circumferences in a symmetric fashion with respect to diameter D of the disk. Stick or peg 2 with a 5 mm diameter is fixed onto disk 1 at the points that coincide with the intersections between the inner circumference and diameter D of said disk.

As it was already mentioned, stick or peg 2 can be of different lengths, and its length preferably ranges between 10 and 100 mm.

Obviously the above dimensions are only indicative, therefore they can well be changed by those skilled in the art in order to suit them to the specific utilisation needs.

Finally, it is useful to observe that from the experiments conducted on adult and child patients, including babies and toddlers, the percentage of success in the induction of a prompt recovery from hiccoughs was 100% in adults and 98% in children. These results are a clear evidence of the validity of the device object of the present invention and of the scope of the present patent.

What is claimed is:

1. A device for the induction of a prompt recovery from hiccoughs, comprising:

a circular disk, provided with a plurality of holes; and a straight cylindrical stick or peg fixed to the disk;

the axes of the disk and of the stick or peg being parallel and not coinciding;

the holes allowing passage of liquids through the disk, in order to generate turbulences and air sacks.

2. The combination of a drinking glass and the device according to claim 1, wherein the device is placed in the glass and the disk contacts the bottom of the glass only with a part of its circumference.

3. The combination of a feeding-bottle and the device according to claim 1, the feeding-bottle having a base, a mouth and a nipple, wherein the stick or peg is introduced into the feeding-bottle and the disk is located between the base of the nipple and the mouth of the bottle.

4. The device according to claim 1, wherein the disk has a 36 mm diameter, 1 mm thickness and 14 holes with 5 mm diameter which are located along two concentric circumferences and symmetrically with respect to the diameter of the disk; the stick having a 5 mm diameter, being fixed to the disk in correspondence with one of the intersections between the inner circumference and the diameter.

5. The device according to claim 1, wherein the stick or peg has a length ranging between 10 and 100 mm.

* * * * *